(12) United States Patent
Eikenberry et al.

(10) Patent No.: US 11,493,385 B2
(45) Date of Patent: Nov. 8, 2022

(54) PORTABLE SPECTROGRAPH FOR HIGH-SPEED PHENOTYPING AND PLANT HEALTH ASSESSMENT

(71) Applicant: University of Florida Research Foundation, Inc., Gainesville, FL (US)

(72) Inventors: Stephen Scott Eikenberry, Gainesville, FL (US); Md. Ali Babar, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1163 days.

(21) Appl. No.: 16/067,915

(22) PCT Filed: Jan. 12, 2017

(86) PCT No.: PCT/US2017/013109
§ 371 (c)(1),
(2) Date: Jul. 3, 2018

(87) PCT Pub. No.: WO2017/123701
PCT Pub. Date: Jul. 20, 2017

(65) Prior Publication Data
US 2020/0264045 A1    Aug. 20, 2020

Related U.S. Application Data

(60) Provisional application No. 62/277,551, filed on Jan. 12, 2016.

(51) Int. Cl.
*G01J 3/00* (2006.01)
*G01J 3/02* (2006.01)
(Continued)

(52) U.S. Cl.
CPC ............ *G01J 3/0256* (2013.01); *G01N 21/84* (2013.01); *G01N 33/0098* (2013.01);
(Continued)

(58) Field of Classification Search
CPC ...... G01J 3/02; G01J 3/28; G01J 3/42; G01N 21/31; G01N 21/552
(Continued)

(56) References Cited

U.S. PATENT DOCUMENTS 6,646,264 B1    11/2003    Modiano et al.
2007/0218657 A1*    9/2007    Bet ................... H01L 21/02683
438/479
(Continued)

FOREIGN PATENT DOCUMENTS

WO    WO 2005/111583 A1    11/2005
WO    WO 2007/129648 A1    11/2007

OTHER PUBLICATIONS

Consumer Physics, SCiO Sensor, May 2, 2014 to Apr. 21, 2018, Internet Archive <https://web.archive.org/web/20140502090326/http://www.consumerphysics.com/myscio/>, 5 pages.
(Continued)

*Primary Examiner* — Md M Rahman
(74) *Attorney, Agent, or Firm* — Alston & Bird LLP (57) ABSTRACT

Embodiments of the present invention are directed to lightweight, portable spectrograph systems configured for applications in high-throughput crop phenotyping and plant health assessment, and associated methods.

20 Claims, 7 Drawing Sheets

(51) Int. Cl.
*G01N 21/84* (2006.01)
*G01N 33/00* (2006.01)

(52) U.S. Cl.
CPC ............ *G01N 2021/8466* (2013.01); *G01N 2201/0221* (2013.01); *G01N 2201/0833* (2013.01)

(58) Field of Classification Search
USPC ...................................................... 356/300
See application file for complete search history.

(56) References Cited

U.S. PATENT DOCUMENTS

2009/0161102 A1  6/2009  Deppermann et al.
2012/0293801 A1  11/2012  Kanai et al.

OTHER PUBLICATIONS

International Searching Authority, International Search Report and Written Opinion for International Application No. PCT/US2017/013109, 12 pages, Korean Intellectual Property Office, Republic of Korea.

* cited by examiner

LOCATION: 44°54'48"N 93°30'12"W – FIELD ABC MINNETONKA, MN
TIMESTAMP: AUGUST 9, 2015 2:02PM CST
ILLUMINATION PARAMETERS: ILLUMINATED BY SUN – 92,762 LUX

PHENOTYPE MEASUREMENT INFORMATION:

CANOPY TEMPERATURE:

CHLOROPHYLL CONTENT:

WATER STRESS:

WATER CONTENT AT CANOPY LEVEL:

NITROGEN STRESS:

GREEN AREA RETENTION:

LEAF WATER POTENTIAL:

SOIL WATER POTENTIAL:

DROUGHT TOLERANT LINES:

OVERALL HEALTHY PLANT GROWTH:

PRODUCTIVITY/YIELD:

PORTABLE SPECTROGRAPH FOR HIGH-SPEED PHENOTYPING AND PLANT HEALTH ASSESSMENT

CROSS REFERENCE TO RELATED APPLICATIONS

This application is a National Stage Application, filed under 35 U.S.C. § 371, of International Application No. PCT/US2017/013109, filed Jan. 12, 2017, which International Application claims priority to and the benefit of United States Provisional Application No. 62/277,551, filed Jan. 12, 2016; the contents of both of which as are hereby incorporated by reference in their entirety herein.

BACKGROUND

Assessing the phenotype and plant health of crops or other plants may provide helpful information for farmers, forestry managers, nurseries, and the like. For example, assessing the phenotype and plant health of crops or other plants may provide information regarding how to encourage crops or other plants to grow well, how to encourage crops or other plants to produce a strong yield, and/or may guide the development of cultivars that are customized to meet the needs of growers in specific environments and climatic locales.

Thus, there is a need for systems, apparatus, and methods for assessing the phenotype and plant health of crops or other plants.

BRIEF SUMMARY

Various embodiments of the present invention relate to a portable spectrograph for high-speed phenotyping and plant health assessment and associated methods. In particular, various embodiments provide methods for analyzing the spectra captured by the portable spectrograph.

BRIEF DESCRIPTION OF THE FIGURES

Having thus described the invention in general terms, reference will now be made to the accompanying drawings, which are not necessarily drawn to scale, and wherein:

DETAILED DESCRIPTION OF VARIOUS EMBODIMENTS

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

I. GENERAL OVERVIEW

Figure 1:
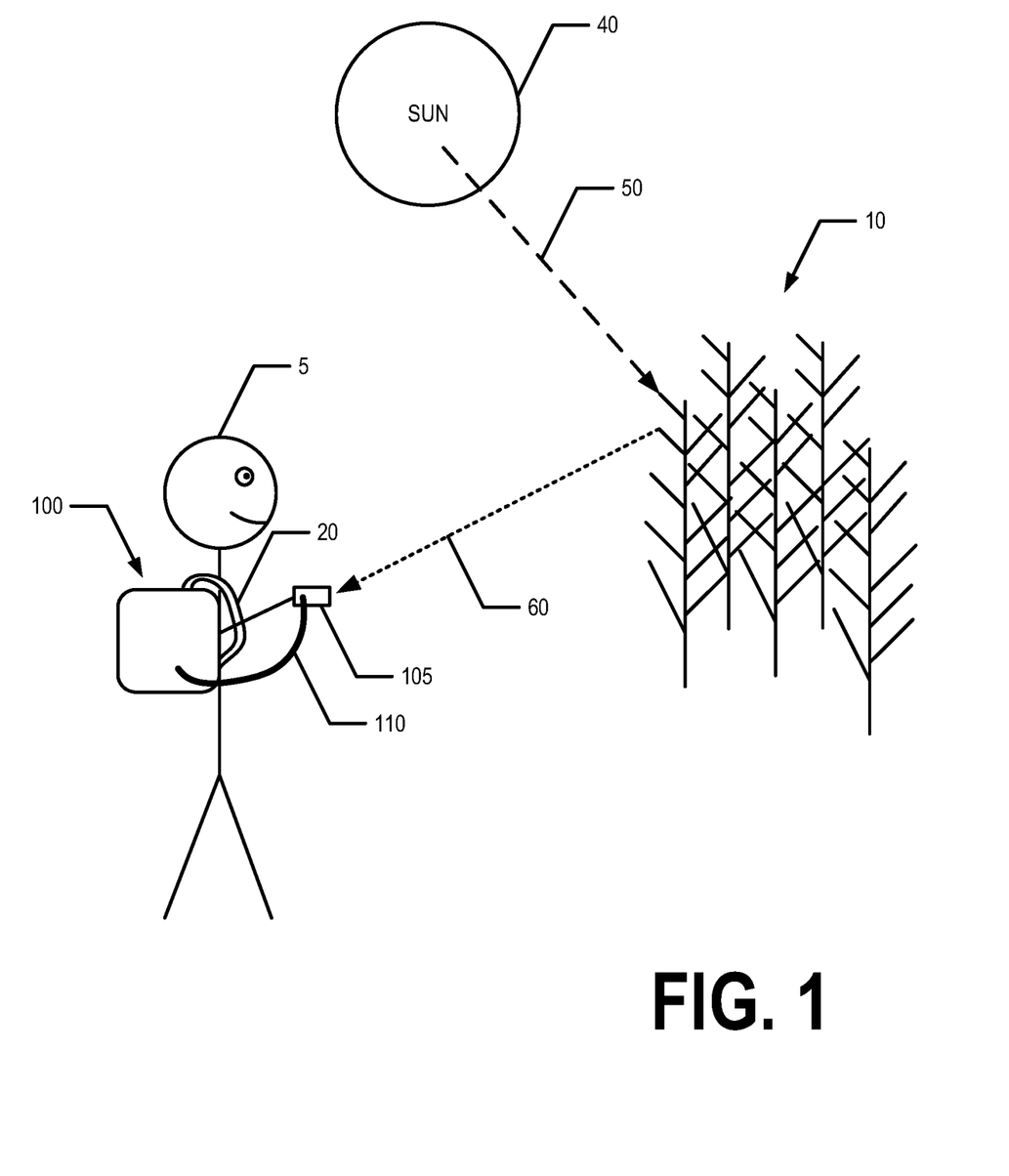
FIG. 1 shows an example spectrograph system in use, in accordance with various embodiments of the present invention.

FIG. 1 provides an illustration of a user 5 using a spectrograph system 100 to capture light reflected off of a crop, plant, or group of plants 10 (referred to as plants herein for simplicity). For example, the sun 40 may emit sunlight 50 that is incident upon plants 10. The reflected light 60 may be captured by a user 5 using a spectrograph system 100. For example, the user 5 may point the spectra capturing device 105 toward the plants 10, such that the reflected light 60 is incident upon an aperture 102 (shown in FIG. 2) of the spectra capturing device 105. The spectrograph 120 of the spectrograph system 100 may condition the reflected light 60 and capture the spectra of the reflected light 60. For example, the spectrograph 120 may disperse the reflected light 60 into spectra and focus the spectra onto the focal plane of a detector 128. The detector 128 may capture the spectra incident thereon and generate a digital representation of the spectra. These raw digital spectra may then be analyzed to extract/determine one or more characteristics of the plants 10.

II. EXEMPLARY PORTABLE SPECTROGRAPH

Figure 2:
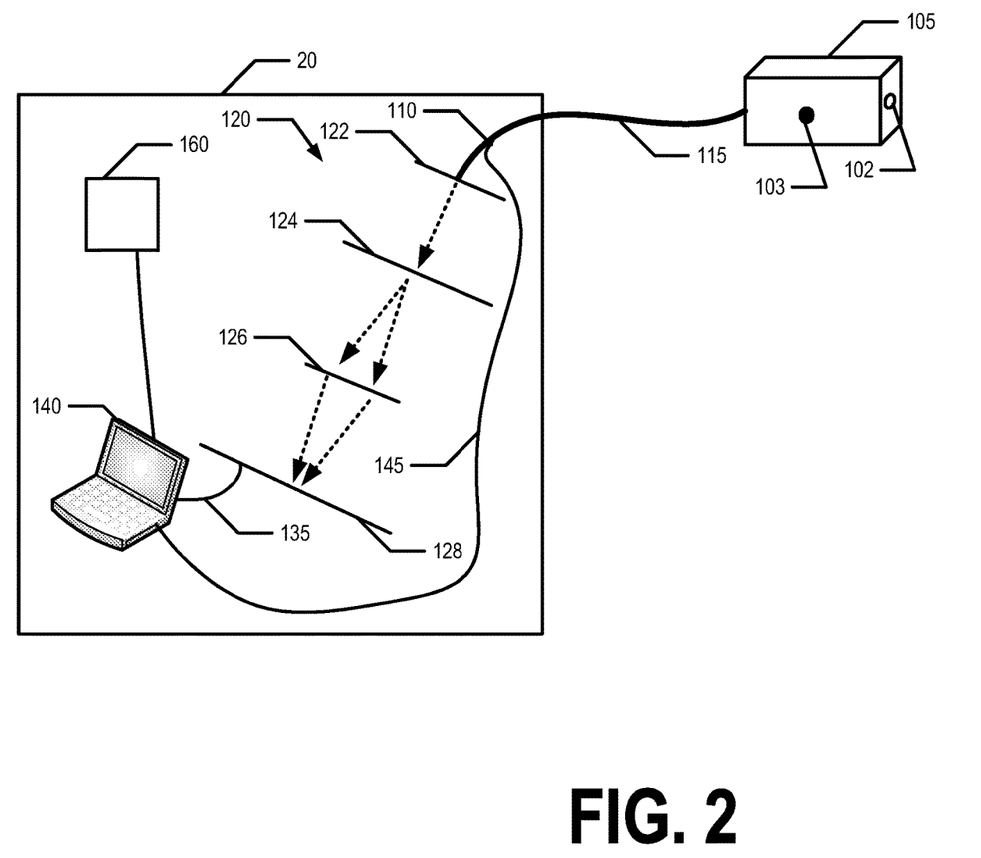
FIG. 2 is a block diagram of a portable spectrograph in accordance with various embodiments of the present invention.
Figure 3:
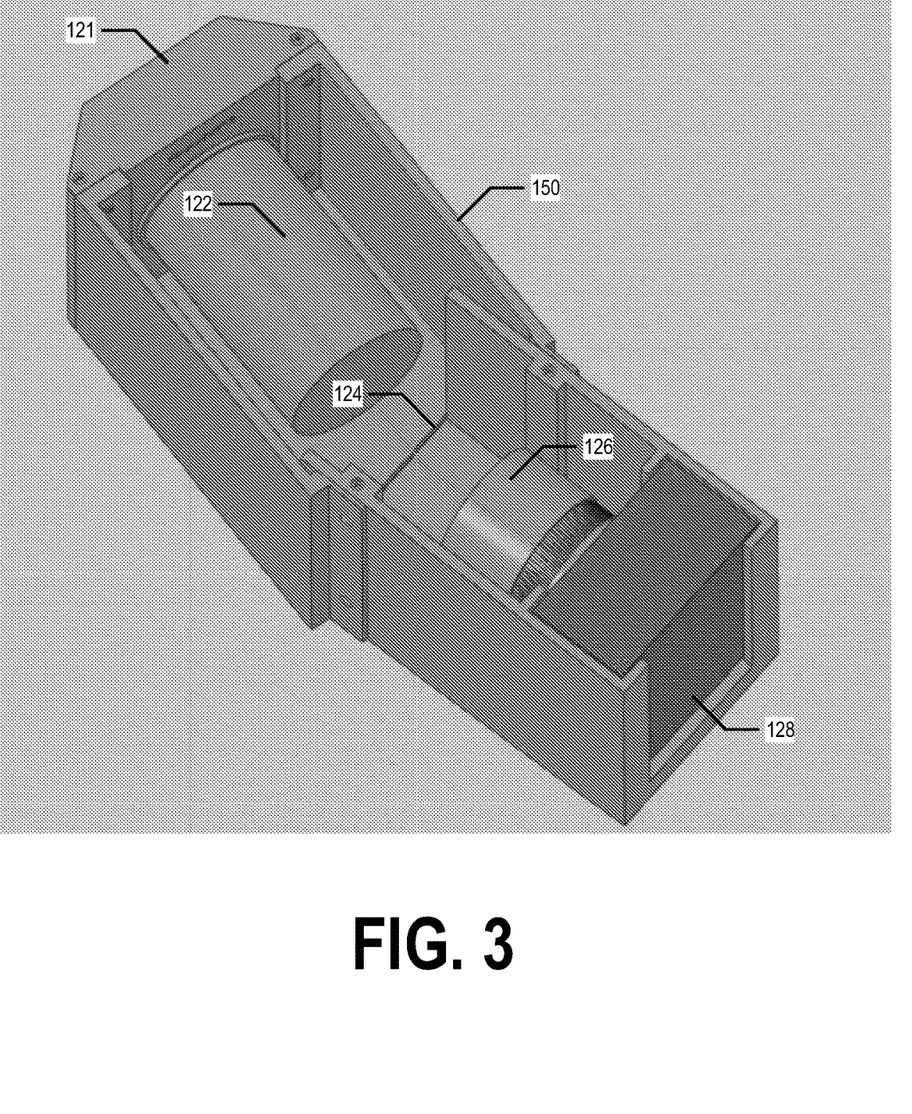
FIG. 3 illustrates an example mechanical layout of the optical components of the portable spectrograph, in accordance with various embodiments of the present invention.
Figure 4:
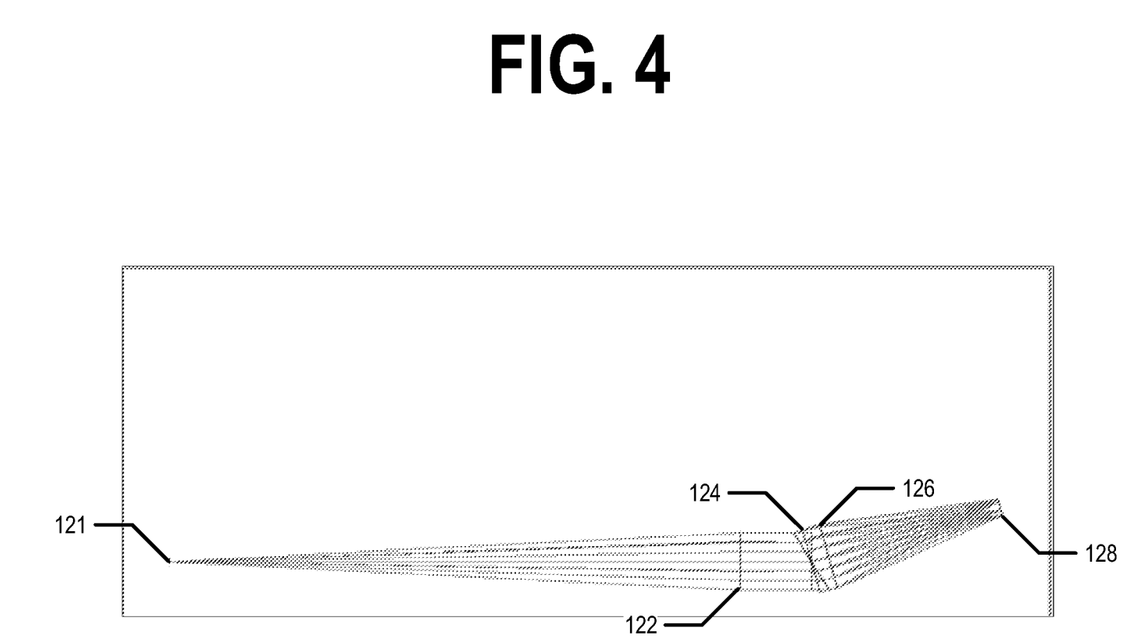
FIG. 4 is a ray diagram of the optical path of the portable spectrograph, in accordance with various embodiments of the present invention.

FIG. 2 provides a block diagram of a spectrograph system 100. The spectrograph system 100 may be a portable, lightweight optical and/or near infrared spectrograph for applications in high-throughput phenotyping of plants 10 and/or determining other characteristics of plants 10. FIG. 3 illustrates and example mechanical layout of the spectrograph 120. Additionally, FIG. 4 provides a ray diagram of an embodiment of the spectrograph 120. Various features of the spectrograph system 100 will now be described with reference to FIGS. 2, 3, and 4.

In various embodiments, a spectrograph system 100 may be configured to be easily portable and easy for a single user to carry and use the spectrograph system, even in remote areas. For example, the spectrograph system 100 may be configured to provide the user with one or more characteristics of a target (e.g., plants 10) in real-time or near real-time. For example, the spectrograph system 100 may be configured to be carried in backpack 20. In various embodiments, the spectrograph system 100 may weigh approximately 10 pounds or less.

In various embodiments, the spectrograph system 100 may comprise a spectra capture device 105, a cable bundle 115 comprising a fiber optical bundle 110 and a control cable 145, spectrograph 120, analysis system 140, location sensor 160, and/or the like.

In various embodiments, the spectrograph system 100 may comprise a spectra capture device 105. In various embodiments, the spectra capture device 105 may be a handheld unit. For example, the spectra capture device 105 may be similar to a grocery store handheld scanner in approximate size and/or shape. The spectra capture device 105 comprises an aperture 102 such that reflected light 60 reflected off of the plants 10 may be incident upon the aperture 102. An objective lens positioned within and/or in line with aperture 102 focuses the reflected light 60 onto a fiber optic bundle 110. The fiber optic bundle 110 may be configured to provide the reflected light 60 to the spectrograph 120. The spatial resolution of the reflected light 60 provided to the fiber optic bundle 110 may be approximately 0.1 to 1.5 mm. The magnification of the objective lens may be selectable such that the magnification for a particular application may be selected based on the distance between the user 5 and the plants 10, and/or the like. It should be understood that the field of view is a function of the magnification of the objective lens and the size of the fiber optic bundle 110. In various embodiments, the field of view is 3 to 10 times the spatial resolution.

The spectra capture device 105 may further comprise a trigger button 103 for triggering the analysis system 140 to cause the capture of raw spectra. For example, when the user 5 presses/selects/clicks/interacts with the trigger button 103, a signal may be communicated along cable bundle 115 (e.g., through control cable 145) to the analysis system 140. The analysis system 140 may receive the signal indicating the user 5 would like to a capture the spectra of the reflected light 60 incident on the spectra capture device 105. In response to receiving the signal, the analysis system 140 may cause a detector 128 to generate a digital representation of the spectra incident upon the detector 128 as will be described in more detail below. In various embodiments, the spectra capture device 105 may further comprise a single lens reflex (SLR) arrangement such that the user 5 may view the area from which the spectra are to be captured.

As noted above, the fiber optic bundle 110 may be configured to provide the reflected light 60 incident upon the aperture 102 (and the objective lens) to the spectrograph 120. For example, the fiber optic bundle 110 may extend from the spectra capture device 105 through the backpack 20 as part of the cable bundle 115. The fiber optic bundle 110 may then enter the spectrograph housing 150 and provide the reflected light 60 to the entrance slit 121 and/or collimator lens 122 (or to another optical component). After the fiber optic bundle 110 enters the spectrograph housing 150 and/or at the entrance slit 121, the fibers of the fiber optic bundle 110 may fan out into a linear array. In one embodiment, the fiber optic bundle 110 comprises a 7-fiber round-to-linear cable having 100-micron fiber cores.

In various embodiments, the spectrograph 120 comprise an entrance slit 121, a collimator lens 122, a transmission grating 124, an off-axis camera lens 126, and/or a detector 128. For example, the entrance slit 121 may be configured to receive the reflected light 60 from the fiber optical bundle 110. The collimator lens 122 receives the reflected light 60 through the entrance slit 121 and collimates the reflected light 60. The collimated light is then incident upon the transmission grating 124, which disperses the light into spectra. The spectra is incident upon the off-axis camera lens 126 which focuses the spectra onto the focal plane of the detector 128. In one embodiment, the collimator lens 122 creates a 19 mm diameter pupil image of the entrance slit 121 on the transmission grating 124. In one embodiment, the transmission grating has 300 lines/mm and is blazed for 900 nm. The off-axis camera lens 126 focuses the spectra onto the focal plane of the detector 128. In various embodiments, the detector 128 is a charge-coupled device (CCD) camera. In various embodiments, the optical components and detector 128 of the portable spectrograph 100 are configured to provide high-throughput simultaneous spectral intensity measurements over the wavelength range 700 to 1000 nm with spectral resolution of approximately 1.5 nm.

As noted above, the spectrograph system 100 may be configured to be worn as and/or in a backpack 20. Thus, the overall size and weight of the spectrograph system 100 are relatively small. In particular, in the embodiment illustrated FIG. 3, the mechanical layout of the optical components (e.g., entrance slit 121, collimator lens 122, transmission grating 124, off-axis camera lens 126, and detector 128) is approximately 15 by 8 by 6 inches. Depending on the lenses and/or other optical components used, the layout of the optical components may be made to be more compact, as appropriate for the application.

In various embodiments, the spectrograph 120 is housed within spectrograph housing 150. In various embodiments, the spectrograph housing 150 is configured to secure the optical components within the spectrograph system 100 (e.g., within backpack 20) such that the optical components are secured with relation to one another and the optical path of the spectrograph 120. For example, the optical component support(s) 150 may be configured to maintain the spatial relationship and orientation of the optical components (e.g., collimator lens 122, transmission grating 124, off-axis camera lens 126, and the detector 128) with respect to each other, thereby maintaining the optical path of the spectrograph 120 and the alignment thereof. In various embodiments, the spectrograph housing 150 comprises optical component supports configured to support individual optical components. In various embodiments, the spectrograph housing 150 may be formed by 3D plastic printing. In various embodiments, the spectrograph housing 150 and/or any optical component supports may be formed by 3D plastic printing. In other embodiments, the spectrograph housing 150 and/or any optical component supports may be formed via another manner that can provide a lightweight and resilient housing and/or optical component supports.

In various embodiments, the detector 128 is configured to capture the spectra focused onto the focal plane of the detector and generate digital representations of the captured spectra. These raw digital spectra are then analyzed by an analysis system to extract/determine one or more characteristics of the target (e.g., the plants 10) off of which the reflected light 60 was reflected. In various embodiments, the detector 128 is in communication with the analysis system 140 via a wired connection 135. For example, the wired connection 135 may be facilitated by a USB cable, Ethernet cable, a custom or off the shelf pinned cable (e.g., VGA cable, etc.), and/or the like. In various embodiments, the analysis system 140 may be a tablet computer or other compact, lightweight computer. The analysis system 140 is described in more detail below.

The analysis system 140 may further be in communication with a trigger button 103 positioned on the spectra capture device 105 via control cable 145. The control cable 145 may be configured to provide a signal to the analysis system 140 that the user would like to capture the spectra incident upon the aperture 102. The analysis system 140 may receive the signal and trigger the detector 128 to generate a digital representation of the spectra focused on the focal plane of the detector 128. In some embodiments, the spectra capture device 105 may comprise a display configured to display one or more characteristics of the target (e.g., plants 10) to the user in real-time or near real-time with respect to the user clicking/selecting/pressing/interacting with the trigger button 103. Thus, the analysis system 140, in response to receiving a signal indicating the user clicking/selecting/pressing/interacting with the trigger button 103, may cause the detector 128 to generate a digital representation of the spectra focuses on the focal plane thereof, analyze the spectra to extract/determine one or more characteristics of the target, and provide the one or more characteristics. In various embodiments, providing the one or more characteristics may comprise at least one of displaying the one or more characteristics via a display associated with the analysis system 140, causing display of the one or more characteristics via a display positioned on the spectra capture device 105 (e.g., transmit a signal indicating the one or more characteristics of the target via the control cable 145), printing or causing the printing of a hardcopy of the one or more characteristics, store the one or more characteristics of the target to be displayed and/or accessed at a later time, transmitting the one or more characteristics via a wired or wireless network for display, storage, and/or processing by a remote computing device, and/or the like.

According to various embodiments, the spectrograph system 100 may include location determining aspects, devices, modules, functionalities, and/or similar words used herein interchangeably (e.g., location sensor 160). For example, the location sensor 160 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information can be determined by triangulating the location sensor's 160 position in connection with a variety of other systems, including wireless towers, Wi-Fi access points, and/or the like. Similarly, the location sensor 160 may include various other positioning aspects, such as a location module adapted to acquire, for example, latitude, longitude, altitude, geocode, course, direction, heading, speed, time, date, and/or various other information/data. Some of the systems may use various position or location technologies including RFID tags, beacons or transmitters, Wi-Fi access points, wireless towers, nearby computing devices (e.g., smartphones, laptops) and/or the like. These positioning aspects can be used in a variety of settings to determine the location of someone or something to within inches or centimeters. In various embodiments, the location sensor 160 may be a component of the analysis system 140 or an independent component of the spectrograph system 100.

In various embodiments, the location sensor 160 may provide accurate time/location meta-data to the analysis system 140. The analysis system 140 may store at least a portion of the time/location meta-data as headers in the spectral images stored on the analysis system 140.

In various embodiments, the spectral system 100 may comprise other and/or different components from those described herein, as appropriate for the application. It should be understood that a variety of spectrographs 120 or other system components may be incorporated into lightweight, portable spectrograph system 100.

III. EXTRACTING/DETERMINING CHARACTERISTICS OF THE TARGET

Figure 5:
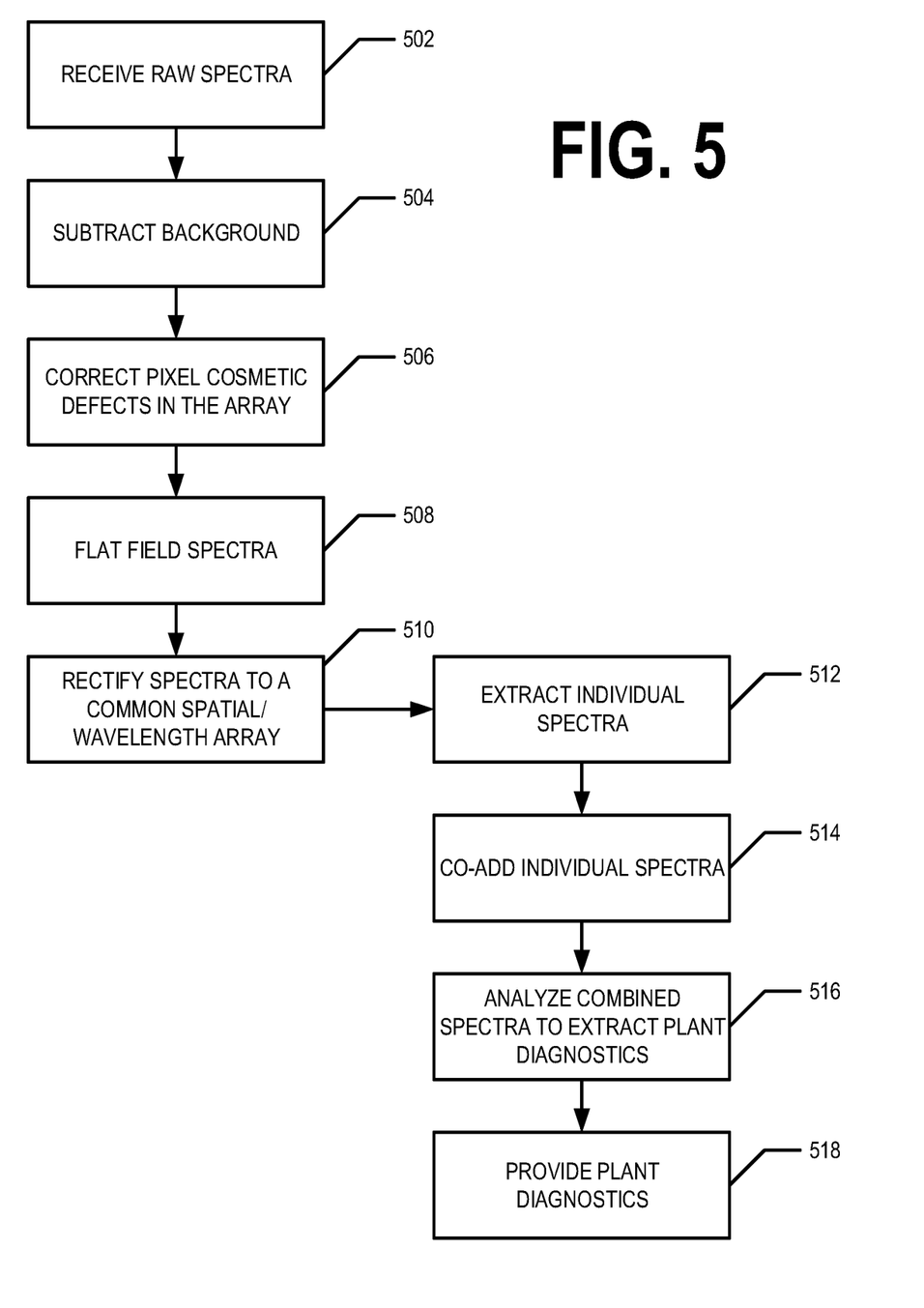
FIG. 5 is a flowchart illustrating various process and procedures that may be used to analyze captured spectra.

FIG. 5 provides a flowchart of processes and procedures that may be used to analyze the raw spectra (e.g., the digital representation of the spectra focused onto the focal plane of the detector 128 generated by the detector 128 and provided to the analysis system 140). In various embodiments, the analysis of the raw spectra may be automated. Starting at step 502, the raw spectra is received. For example, the analysis system 140 may receive the raw spectra. For example, the user may click/select/press/interact with the trigger button 103, causing the analysis system 140 to trigger the detector 128 to generate a digital representation of the spectra focused on the focal plane of the detector 128. The analysis system 140 then receives the digital representations of the spectra from the detector 128. The received digital representations may be stored as raw spectra. In various embodiments, receiving the raw spectra/digital representations of the spectra may cause the analysis system 140 to perform an automated and autonomous analysis of the raw spectra to calibrate the spectra and determine/extract one or more characteristics of the target (e.g., plants 10).

At step 504, the background is subtracted from the raw spectra. For example, the analysis system 140 may use an algorithm, software module, and/or the like to subtract the background from the raw spectra. At step 506, the background subtracted spectra are corrected for pixel cosmetic defects in the array. For example, the analysis system 140 corrects the background subtracted spectra for pixel cosmetic defects in the array. For example, the detector 128 focal plane array may cause one or more pixel cosmetic defects in the digital representations of the spectra focused on the focal plane of the detector 128. The analysis system 140 may execute an algorithm, software module, and/or the like to correct the pixel cosmetic defects in the background subtracted spectra.

At step 508, the corrected spectra are flat-fielded. For example, the analysis system 140 may flat field the corrected spectra. For example, the corrected spectra may be calibrated via a flat fielding technique. At step 510, the flat-fielded spectra are rectified to a common spatial/wavelength array. For example, the analysis system 140 may rectify the flat-fielded spectra to a common spatial/wavelength array. For example, the flat-fielded spectra may be rectified to a common spatial/wavelength array to make the subsequent combining spectra a more straight forward process.

At step 512, individual spectra are extracted. For example, the analysis system may extract individual spectra from the rectified spectra. In various embodiments, the individual spectra may be spectra captured by various fibers of the fiber optic bundle, spectra corresponding to various regions of the field of view of the aperture/objective lens 102, and/or the like. At step 514, the individual spectra are co-added or combined. For example, the analysis system 140 may co-add or combine the individual spectra to form a combined spectra. In various embodiments, the individual spectra are co-added or combined using optimal pixel-weighted schemes. For example, the individual spectra may be co-added or combined using pixel-weighted schemes that provide a maximum signal-to-noise spectrum of the target (e.g., plants 10).

At step 516, the combined spectra are analyzed to extract/determine one or more characteristics of the target (e.g., plants 10). For example, the analysis system 140 may analyze the combined spectra to extract/determine one or more characteristics of the target. For example, the intensities of key spectral plant features may be extracted/determined from the combined spectra. For example, the intensity of features at 550 nm, 680 nm, 780 nm, 850 nm, 880 nm, 900 nm, 970 nm, and/or the like may be extracted/determined from the combined spectra. For example, the spectral continuum of the combined spectra may be fit with a template absorption profiles (e.g., determined from laboratory samples), to determine the intensity of the spectral features. In various embodiments, deviations of the template fit to the actual combined spectra data may be measured and stored in order to provide automated data quality assessment. In various embodiments, the relative strength of the 970 nm and the 900 nm, the 970 nm and the 850 nm, and the 970 nm and 880 nm features may be considered. For example, in one embodiment, the analysis system 140 may determine/calculate the values:

$$NW_{i\text{-}1}=[R_{970}-R_{900}]/[R_{970}+R_{900}]$$

$$NW_{i\text{-}2}=[R_{970}-R_{850}]/[R_{970}+R_{850}],$$

$$NW_i=[R_{970}-R_{880}]/[R_{970}-R_{880}]$$

wherein $R_x$ is the intensity of the spectral feature at wavelength x.

In various embodiments, the one or more characteristics extracted/determined from the combined spectra may be related to the phenotype of the target (e.g., plants 10) and/or key health indices that may be used by agronomists to evaluate crop productivity and yield early in the plant life cycle. The extracted/determined characteristic(s) may also be use dot provide corrective care to the target (e.g., plants 10) (e.g., nutrients, water, etc.) to maximize crop yield. In various embodiments, the one or more extracted/determined characteristics may comprise canopy temperature, chlorophyll content, water stress, water content at canopy level, nitrogen stress, green area retention, leaf water potential, soil water potential, drought tolerance lines, over healthy plant growth, productivity/yield, and/or the like. Thus, the analysis of the reflected light 60 may provide indirect assessments of one or more characteristics of the target (e.g., plants 10).

Figure 6:
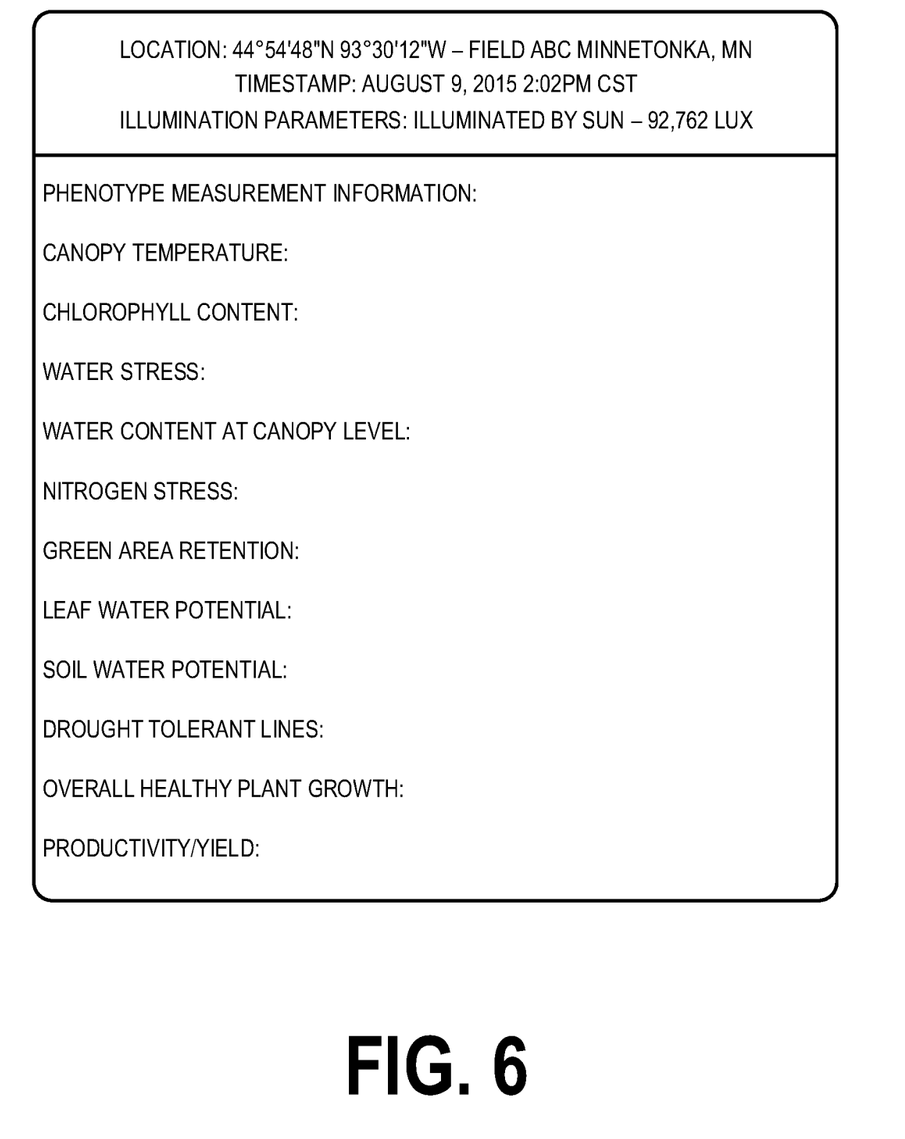
FIG. 6 is an example output view of an example portable spectrograph user interface, in accordance with various embodiments of the present invention.

At step 518, the one or more extracted/determined characteristics of the target are displayed. For example, the analysis system 140 may display or cause the display of at least one of the one or more extracted/determined characteristics. For example, the analysis system 140 may display an interface similar to that shown in FIG. 6 providing at least one of the one or more characteristics of the target (e.g., plants 10). In some embodiments, the analysis system may print or cause the printing of a hard copy of at least one of the one or more characteristics, store the one or more characteristics to be displayed and/or accessed at a later time, transmitting the one or more characteristics via a wired or wireless network for display, storage, and/or processing by a remote computing device, and/or the like. In various embodiments, the at least one of the one or more characteristics may be displayed and/or otherwise provided in real-time and/or near real-time. The one or more characteristics of the target (e.g., plants 10), may be displayed and/or provided in a variety of ways as appropriate for the application.

Thus, in various embodiments, the user may select/click/press/interact with the trigger button 103 causing the spectra to be captured, the digital representation of the spectra to be analyzed, and at least one characteristic of the target (e.g., plants 10) to be displayed and/or otherwise provided in real-time or near real-time. Thus, the user may use the lightweight, portable spectrograph system 100 to assess the health of plants 10 in mere minutes. Moreover, the lightweight, portable spectrograph system 100 may be used by a single user in any terrain and is capable of operation under a wide range of illumination conditions. For example, the simultaneous data acquisition and improved analysis/extraction routine may allow a user to use the spectrograph system 100 under a wide range of illumination conditions and terrain. Thus, example embodiments of the present invention provide improved techniques for determining characteristics of plants 10 in a timely manner.

IV. EXEMPLARY ANALYSIS SYSTEM 140

Figure 7:
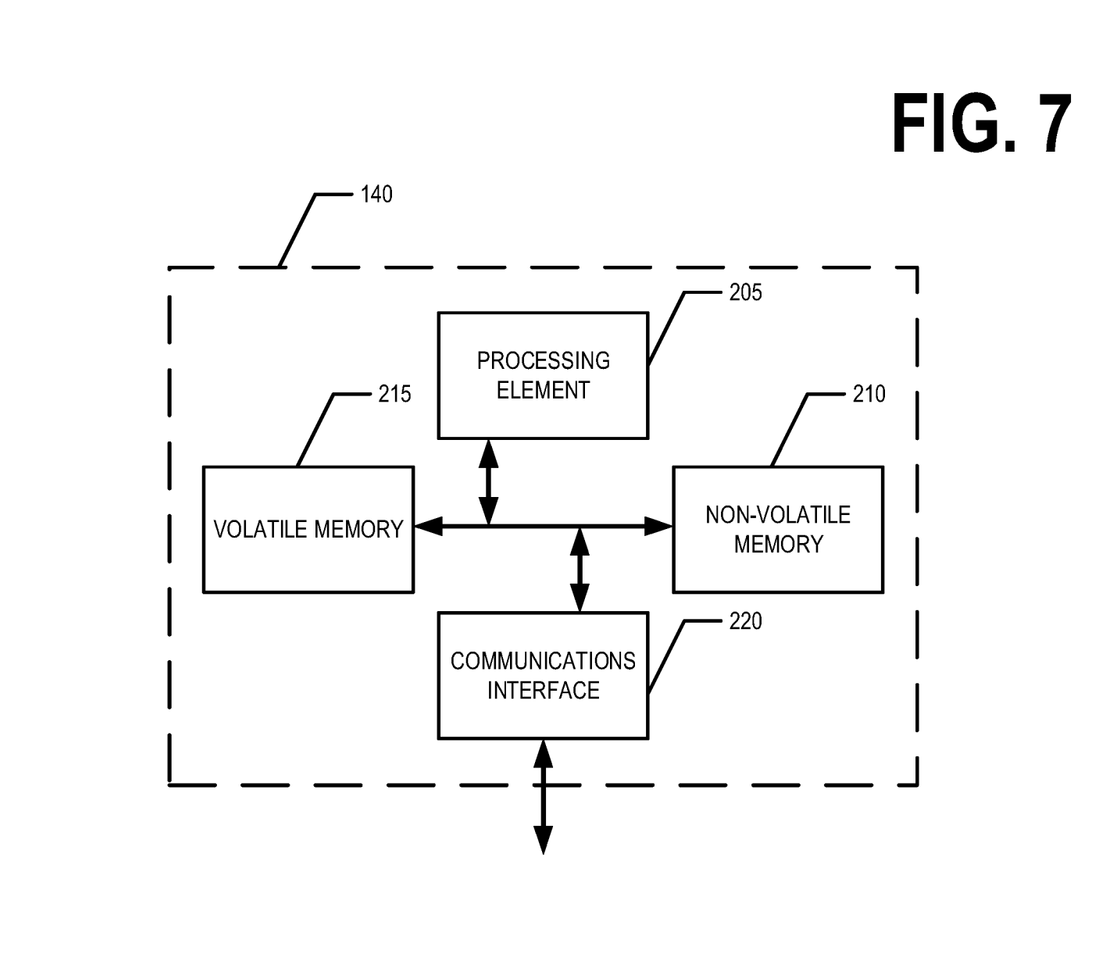
FIG. 7 is block diagram illustrating an example analysis system, in accordance with various embodiments of the present invention.

FIG. 7 provides a schematic of an analysis system 140 according to one embodiment of the present invention. In general, the terms computing entity, computer, entity, device, system, and/or similar words used herein interchangeably may refer to, for example, one or more computers, computing entities, mobile phones, tablets, phablets, notebooks, laptops, distributed systems, wearable computing devices, processing devices, processing entities, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably. In various embodiments, the analysis system 140 is a mobile computing device such as a tablet.

As indicated, in one embodiment, the analysis system 140 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 7, in one embodiment, the analysis system 140 may include or be in communication with one or more processing elements 205 (also referred to as processors, processing circuitry, and/or similar terms used herein interchangeably) that communicate with other elements within the analysis system 140 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the analysis system 140 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the analysis system 140 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the carrier/transporter computing entity 100 with the assistance of the processing element 205 and operating system.

As indicated, in one embodiment, the analysis system 140 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the carrier/transporter computing entity 100 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), infrared (IR) protocols, near field communication (NFC) protocols, Wibree, Bluetooth protocols, wireless universal serial bus (USB) protocols, and/or any other wireless protocol.

Although not shown, the analysis system 140 may include or be in communication with one or more input elements, such as a keyboard input, a mouse input, a touch screen/display input, motion input, movement input, audio input, pointing device input, joystick input, keypad input, and/or the like. The analysis system 140 may also include or be in communication with one or more output elements (not shown), such as audio output, video output, screen/display output, motion output, movement output, and/or the like.

As will be appreciated, one or more of the analysis system 140 may be located remotely from other analysis system 140 components, such as in a distributed system. Furthermore, one or more of the components may be combined and additional components performing functions described herein may be included in the analysis system 140. For example, the position sensor 160 may be a component of the analysis system 140. Thus, the analysis system 140 can be adapted to accommodate a variety of needs and circumstances. As will be recognized, these architectures and descriptions are provided for exemplary purposes only and are not limiting to the various embodiments.

V. COMPUTER PROGRAM PRODUCTS, METHODS, AND COMPUTING ENTITIES

Embodiments of the present invention may be implemented in various ways, including as computer program products that comprise articles of manufacture. A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

VI. CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims Although specific terms are employed herein, they are used in a generic and descriptive sense only and not for purposes of limitation.

The invention claimed is:

1. A spectrograph system comprising:
a spectra capture device comprising a housing having an aperture therein and a lens disposed within the housing and aligned with the aperture, the spectra capture device configured to have reflected spectra incident on the lens through the aperture such that the lens provides the reflected spectra to an optical fiber, the reflected spectra being a spectra that is reflected off of a target;
at least one optical component configured to receive the reflected spectra from the optical fiber and condition the reflected spectra;
a detector configured to have the conditioned reflected spectra incident thereon and generate digital representations thereof; and
an analysis system configured to receive the digital representations and analyze the digital representations to determine one or more characteristics of the target,
wherein the spectrograph system is configured to be fitted within a back pack and worn on a user's back and the spectra capture device is configured to be held in the user's hand.

2. The spectrograph system of claim 1, wherein the target is a crop and/or one or more plants.

3. The spectrograph system of claim 1, wherein the reflected spectra is sunlight that is reflected off of the target.

4. The spectrograph system of claim 1, wherein the at least one optical component comprises a collimator lens, a transmission grating, and an off-axis camera lens.

5. The spectrograph system of claim 1, wherein the at least one optical component is at least one of supported or secured by a corresponding optical support, the optical support being a light weight optical support formed by three-dimensional (3D) printing.

6. The spectrograph system of claim 1, wherein the analysis system comprises a processing element and one or more non-transitory computer-readable storage elements, the one or more computer-readable storage elements storing computer-readable instructions which, when executed by the one or more processing elements, causes the processing elements to automatically analyze the digital representations.

7. The spectrograph system of claim 6, wherein the computer read-able instructions comprise at least one of: instructions for background subtraction, pixel cosmetic defect correction, flat fielding, rectifying the digital representations to a common spatial/wavelength array, extracting individual spectra, co-adding individual spectra, and analyzing the co-added individual spectra to extract characteristics of the target.

8. The spectrograph system of claim 6, wherein:
the analysis system comprises a display, and
the computer-readable instructions, when executed by the one or more processing elements, cause the one or more processing elements to cause the display to display one or more extracted characteristics of the target.

9. The spectrograph system of claim 1, wherein the characteristics of the target comprise at least one of phenotype information, a canopy temperature, chlorophyll content of the target, water stress, water content at canopy level, nitrogen stress, green area retention, leaf water potential, soil water potential, drought tolerant lines, overall healthy plant growth, or productivity/yield.

10. The spectrograph system of claim 1, wherein the analysis system is configured to provide the one or more characteristics in real time or near real time.

11. The spectrograph system of claim 1, wherein:
the spectrograph system weights less than ten pounds, and
the at least one optical component, the detector, and the analysis system are positioned within a backpack such that the spectrograph system is portable and may be used by a single user.

12. A method for extracting characteristics of a target, the method comprising:
receiving raw spectra from a spectrograph system, the raw spectra being reflected from a target;
performing background subtraction on the raw spectra;
correcting pixel cosmetic defects in the background subtracted spectra;
flat fielding the corrected spectra;
rectifying the flat fielded spectra to a common spatial/wavelength array;
extracting individual spectra from the rectified spectra;
co-adding the individual spectra to form combined spectra; and
analyzing the combined spectra to determine one or more characteristics of the target.

13. The method of claim 12, further comprising the step of causing display of the one or more characteristics in real time or near real time with respect to when the raw spectra are received.

14. The method of claim 12, wherein the one or more characteristics comprise at least one of phenotype information, a canopy temperature, chlorophyll content of the target, water stress, water content at canopy level, nitrogen stress, green area retention, leaf water potential, soil water potential, drought tolerant lines, overall healthy plant growth, or productivity/yield.

15. The method of claim 12, wherein the target is at least one of a crop, or one or more plants.

16. The method of claim 12, wherein analyzing the combined spectra comprises analyzing spectral features at least at one of 550 nm, 680 nm, 780 nm, 850 nm, 880 nm, 900 nm, or 970 nm.

17. The method of claim 16, wherein analyzing the spectral features comprises fitting a template absorption profile to the combined spectra to extract the intensity of the spectral features.

18. The method of claim 16, wherein analyzing the spectral features comprises analyzing the relative intensity of at least one of the 970 nm and 900 nm features, the 970 nm and the 850 nm features, or the 970 nm and 880 nm features.

19. The method of claim 12, wherein the spectrograph system further comprises:
a spectra capture device comprising an aperture and a lens disposed within the aperture, the spectra capture device configured to have reflected spectra incident on the lens through the aperture such that the lens provides the reflected spectra to an optical fiber, the reflected spectra being a spectra that is reflected off of a target;
at least one optical component configured to receive the reflected spectra from the optical fiber and condition the reflected spectra;
a detector configured to have the conditioned reflected spectra incident thereon and generate digital representations thereof; and
an analysis system configured to receive the digital representations and analyze the digital representations to determine one or more characteristics of the target,
wherein the spectrograph system weighs less than ten pounds.

20. The method of claim 19, wherein spectrograph system further comprises at least one optical support configured to at least one of secure or support the at least one optical component, the at least one optical support being formed by 3D printing.

* * * * *